US012186339B2

(12) United States Patent
Brier, Jr. et al.

(10) Patent No.: US 12,186,339 B2
(45) Date of Patent: *Jan. 7, 2025

(54) SYSTEM AND METHOD OF USE FOR HALOTHERAPY SESSIONS

(71) Applicants: John J. Brier, Jr., Lithia, FL (US); Edwin A. Weihenmayer, IV, Pensacola, FL (US)

(72) Inventors: John J. Brier, Jr., Lithia, FL (US); Edwin A. Weihenmayer, IV, Pensacola, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/488,151

(22) Filed: Oct. 17, 2023

(65) Prior Publication Data

US 2024/0050467 A1    Feb. 15, 2024

Related U.S. Application Data

(63) Continuation of application No. 16/858,187, filed on Apr. 24, 2020, now Pat. No. 11,819,515.

(Continued)

(51) Int. Cl.
*A61K 33/14*     (2006.01)
*A61K 9/00*      (2006.01)
(Continued)

(52) U.S. Cl.
CPC .......... *A61K 33/14* (2013.01); *A61K 9/0073* (2013.01); *A61M 16/14* (2013.01); *A61N 5/06* (2013.01);
(Continued)

(58) Field of Classification Search
CPC ..... A61K 9/0073; A61K 33/14; A61M 16/14; A61M 16/161; A61M 2202/066;
(Continued)

(56) References Cited

U.S. PATENT DOCUMENTS 4,833,739 A * 5/1989 Sakakibara .......... A61H 33/063
4/524
5,881,720 A * 3/1999 Vinogradov ...... A61M 15/0028
128/200.14

(Continued)

FOREIGN PATENT DOCUMENTS

DE     102008016232 A1 * 10/2009 ............. A61G 10/02
WO    WO-2008092465 A1 * 8/2008 ............. A61K 33/14

*Primary Examiner* — Colin W Stuart
*Assistant Examiner* — Matthew D Ziegler
(74) *Attorney, Agent, or Firm* — David Colls; Berger Singerman LLP

(57) ABSTRACT

A system and method of use for an operational halotherapy device and red light device in an enclosed space. The halotherapy and red light system generally comprise a machine disposed in the enclosed space that disperses salt particles into the air, and includes a red light device that emits red light waves. The combination of both devices produces a refractory phenomenon when the red light waves make contact with the salt particles dispersed in the air to cause a plethora of multi-dimensional dispersions of light waves. Moreover, every time a salt particle makes contact with a red light wave, a portion of the wave light is absorbed by the particle and its temperature increases, lessening the moisture in the particle. The lessening of moisture in the particle dries the particle further, which enhances the therapeutic properties of the inhalable salt particle.

20 Claims, 6 Drawing Sheets

Related U.S. Application Data

(60) Provisional application No. 62/837,751, filed on Apr. 24, 2019, provisional application No. 62/974,137, filed on Nov. 18, 2019.

(51) Int. Cl.
*A61M 16/14* (2006.01)
*A61M 16/16* (2006.01)
*A61N 5/06* (2006.01)

(52) U.S. Cl.
CPC ..... *A61M 16/161* (2014.02); *A61M 2202/066* (2013.01); *A61M 2205/051* (2013.01); *A61M 2205/056* (2013.01); *A61M 2205/3368* (2013.01); *A61M 2250/00* (2013.01); *A61N 2005/0663* (2013.01)

(58) Field of Classification Search
CPC ...... A61M 2205/051; A61M 2205/056; A61M 2205/3368; A61M 2250/00; A61N 5/06; A61N 2005/0663
See application file for complete search history.

(56) References Cited

U.S. PATENT DOCUMENTS

| 9,629,777 B2 * | 4/2017 | Shurtleff | ............... A61H 33/063 |
| 2015/0127076 A1 * | 5/2015 | Johnson | ............... A61N 5/0613 |
| | | | 607/90 |

* cited by examiner

SYSTEM AND METHOD OF USE FOR HALOTHERAPY SESSIONS

CROSS-REFERENCE TO RELATED APPLICATIONS

This continuation application claims the benefit of U.S. nonprovisional patent application Ser. No. 16/858,187, filed on Apr. 24, 2020, claims the benefit of U.S. Provisional Patent Application Ser. No. 62/837,751, filed on Apr. 24, 2019, and claims the benefit of U.S. Provisional Patent Application Ser. No. 62/974,137, filed on Nov. 18, 2019, all of which are incorporated herein in its entirety.

FIELD OF THE INVENTION

The present invention relates generally to systems and methods of use, and more particularly, to a system and method of use of a halotherapy system and red light system that emits red light low-level wavelengths that in combination improve the positive effects sustained during the halotherapy session.

BACKGROUND OF THE INVENTION

Halotherapy or salt therapy is a form of alternative medicine that makes use of salt. Halotherapy involves grinding salt to fine particles and then dispersed into the surrounding air. This form of therapy is typically done in a closed environment, such as a room or booth, where people inside of the closed environment can easily breathe in the air mixture of oxygen, nitrogen and salt particles dispensed in the air. Salt inhalation therapy, or otherwise referred to as halotherapy, is known to benefit individuals who suffer from respiratory illnesses, such as asthma, chronic bronchitis, and allergies. Salt therapy is also known to improve lung health, kill bacteria, treat depression and anxiety and in some cases cure certain skin conditions, such as psoriasis, eczema, and acne.

In addition to health improvements, halotherapy has shown to improve the performance of athletes because it cleans the respiratory system of an athlete, naturally opening the airways, helping to improve lung function and increasing lung capacity. This means that an athlete having undergone such therapy is able to reduce lung exertion and as a result increase their performance endurance.

Aside from halotherapy, other therapeutic techniques can help athletes with their performance and physique. For instance, red light therapy is a therapeutic technique that uses red low-level wavelengths of light to treat skin issues, such as wrinkles, scars, and persistent wounds, among other conditions. In some clinical trials, red light therapy has also shown to increase testosterone levels, as well as reduce symptoms of depression, improve muscle recovery, aid weight loss, reduce inflammation and heal injuries.

Accordingly, there is an established need for a system and method of use for halotherapy treatment that could be combined with other therapeutic techniques, such as red light therapy, to enhance, improve, and increase lung function, testosterone levels, and muscle recovery, while reducing or eliminating symptoms of depression, skin ailments, and other treatable conditions.

SUMMARY OF THE INVENTION

The present invention is directed to a system and method of use for a halotherapy system that also projects red light low-level wavelengths in a closed space. The combination of halotherapy and red light therapy produces a refractory phenomenon as the light waves make contact with the salt particles dispersed in the air to cause a plethora of multi-dimensional dispersions of light waves.

Introducing a first embodiment of the invention, the present invention consists of a halotherapy and red light system, comprising an enclosed space, a machine, and a red light device. The machine may comprise a body comprising a back portion and a front portion, where the front portion includes a control panel and at least one vent. The machine is capable of dispersing salt particles into the surrounding air inside of the enclosed space. The red light device may comprise a body disposed about the ceiling of the enclosed space and include at least one LED that emits red light waves.

In a second aspect, the system may include a physical exertion machine disposed inside of the enclosed space.

In another aspect, the machine may be capable of grinding salt crystals into dispersible salt particles.

In another aspect, the machine may be attached to a designated wall space of the enclosed space.

In another aspect, the physical exertion machine may be one of a stationary cycling machine, rowing machine, walking and running machine, resistance machine, and elliptical machine.

In another aspect, the physical exertion machine may include one of a pulling, pushing, and lifting machine, and a resistance machine.

In another aspect, the red light waves emitted by the red light device are absorbable by a person.

In another aspect, the red light device may emit wavelength beams within a range of about 660 nm to about 850 nm.

In another aspect, at least one red light wave will make contact with at least one salt particle suspended in the air contained inside of the enclosed space. When the wave makes contact with the salt particle, a portion of the red light wave refracts and disperses elsewhere while another portion of the red light wave is absorbed by the salt particle.

In another aspect, the temperature of a salt particle may increase after absorbing a portion of the red light wave that makes contact with the salt particle. The increase in temperature lessens the moisture within the salt particle.

In another aspect, the enclosed space may include a booth, a room, a standing structure, a sauna type room or the like.

In another aspect, the red light waves in the enclosed space may be absorbable by a person and the salt particles are inhalable and absorbable by the person.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
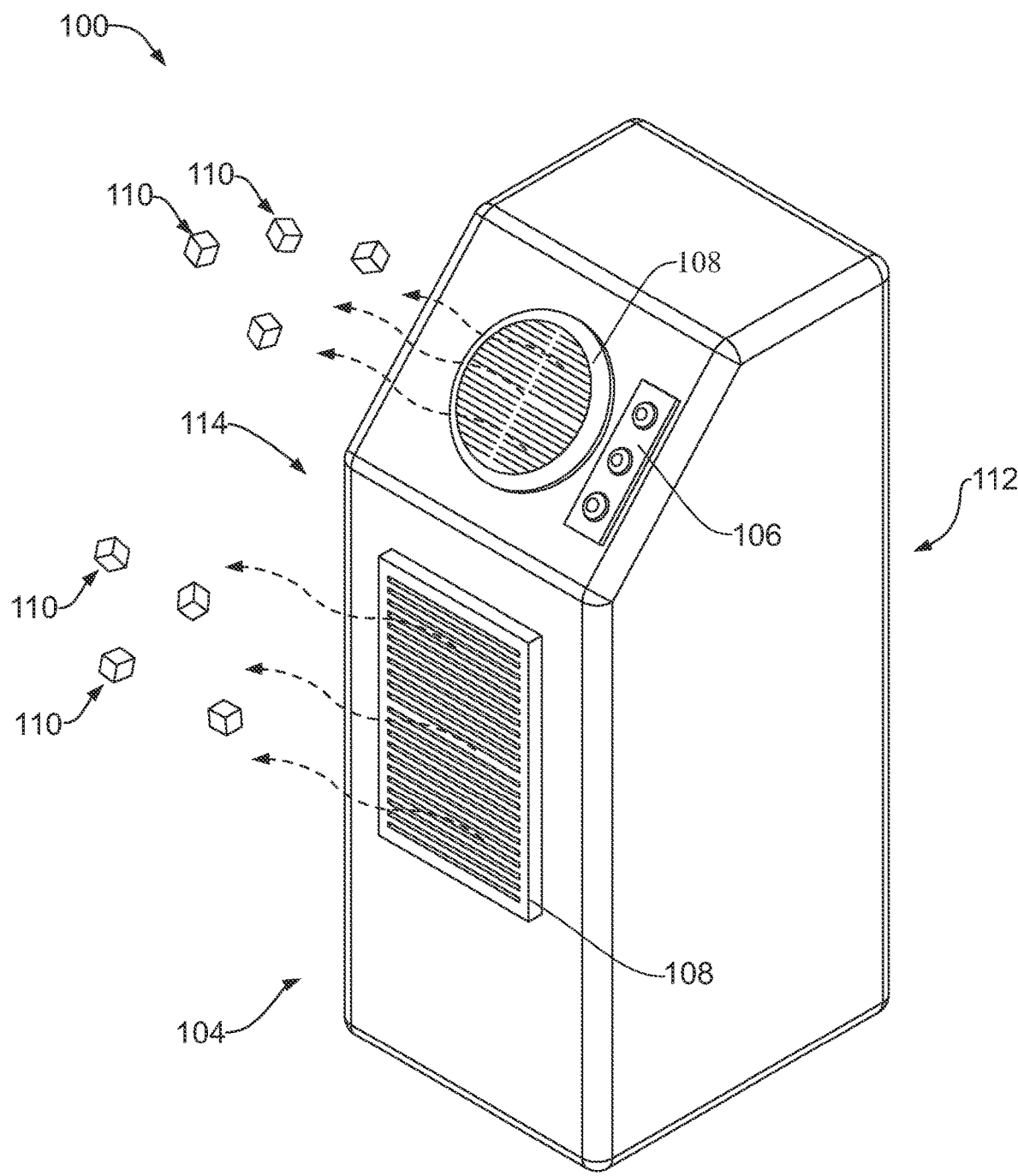
FIG. 1 presents a perspective view showing a halotherapy apparatus used with the system and method of use of the present invention.
Figure 2:
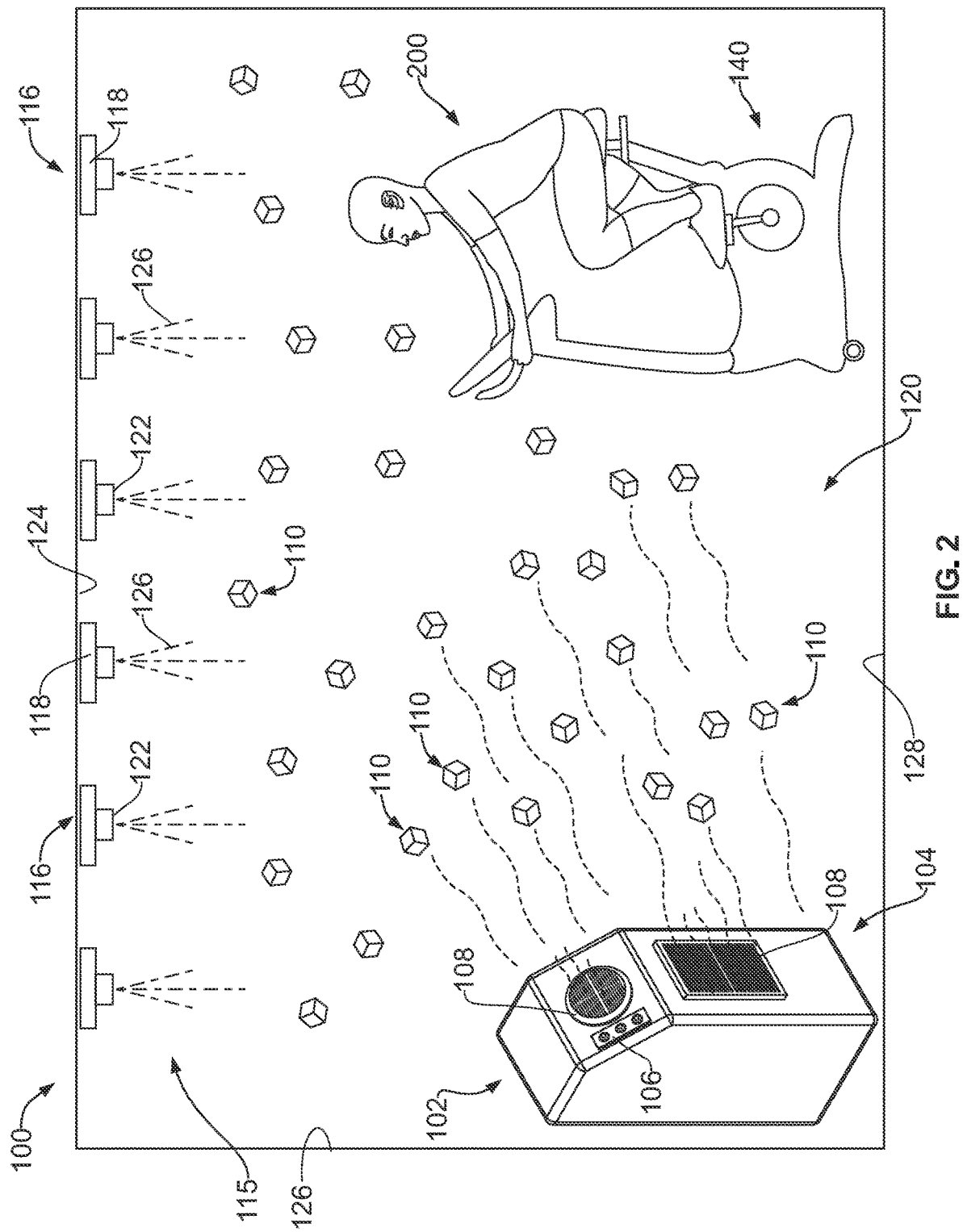
FIG. 2 presents a side view of an enclosed space where red light wave therapy and an exercise machine are used in a halotherapy session in accordance with the system and method of use of the present invention.

Referring initially to FIGS. 1 and 2, an exemplary embodiment of a halotherapy and red light system 100 is generally shown. The halotherapy and red light system 100 may comprise an enclosed space 120, a machine 102, and a red light device 115. The enclosed space 120 may include at least four upstanding sidewalls 126 supporting a ceiling 124. Supporting the upstanding sidewalls 126 may be a floor or a base 128. The enclosed space 120 may also include at least one entry door (not shown) that gives access into the enclosed space 120. In one exemplary form, the enclosed space may be part of a larger structure such as, a room in a building. In that particular embodiment, the enclosed space 120 may include for aesthetic purposes salt-covered walls, special lighting, loose salt floors, and comfortable seating such as, lounge chairs, recliners, sofa, or the like. In another exemplary embodiment, the enclosed space 120 may include sensors that read humidity, moisture and temperature levels. The enclosed space may further include special mood lighting, and have an HVAC system that provides heating and air conditioning to the enclosed space 120.

In another exemplary embodiment, the upstanding sidewalls 126, base 128, and ceiling 124 of the enclosed space may be treated with chemicals to prevent salt from migrating out of the enclosed space. For instance, the surrounding walls, floor and ceiling of the enclosed space 120 may be treated and cured with known sealants to prevent salt particles from escaping or penetrating through the wall material. In another exemplary embodiment, the surrounding walls of the enclosed space 120 may be treated and a layered with salt covered tiles that are adhered to the upstanding sidewalls 126 of the enclosed space 120 to provide an aesthetic look to the space. On the base 128 (or floor) of the enclosed space 120, loose salt may be evenly dispersed across the surface area of the base forming a thick layer of salt on the ground. In yet another embodiment, the enclosed space may be a freestanding structure, such as a booth, tent, a portable trailer, and an erectable or transportable structure. For example, a transportable structure may be transported between locations to service persons in different locals with halotherapy treatments. In that particular case, all that is necessary is that the enclosed space have ventilation. However, it is appreciated that the structure may include some or all of the aforementioned amenities.

Figure 3:
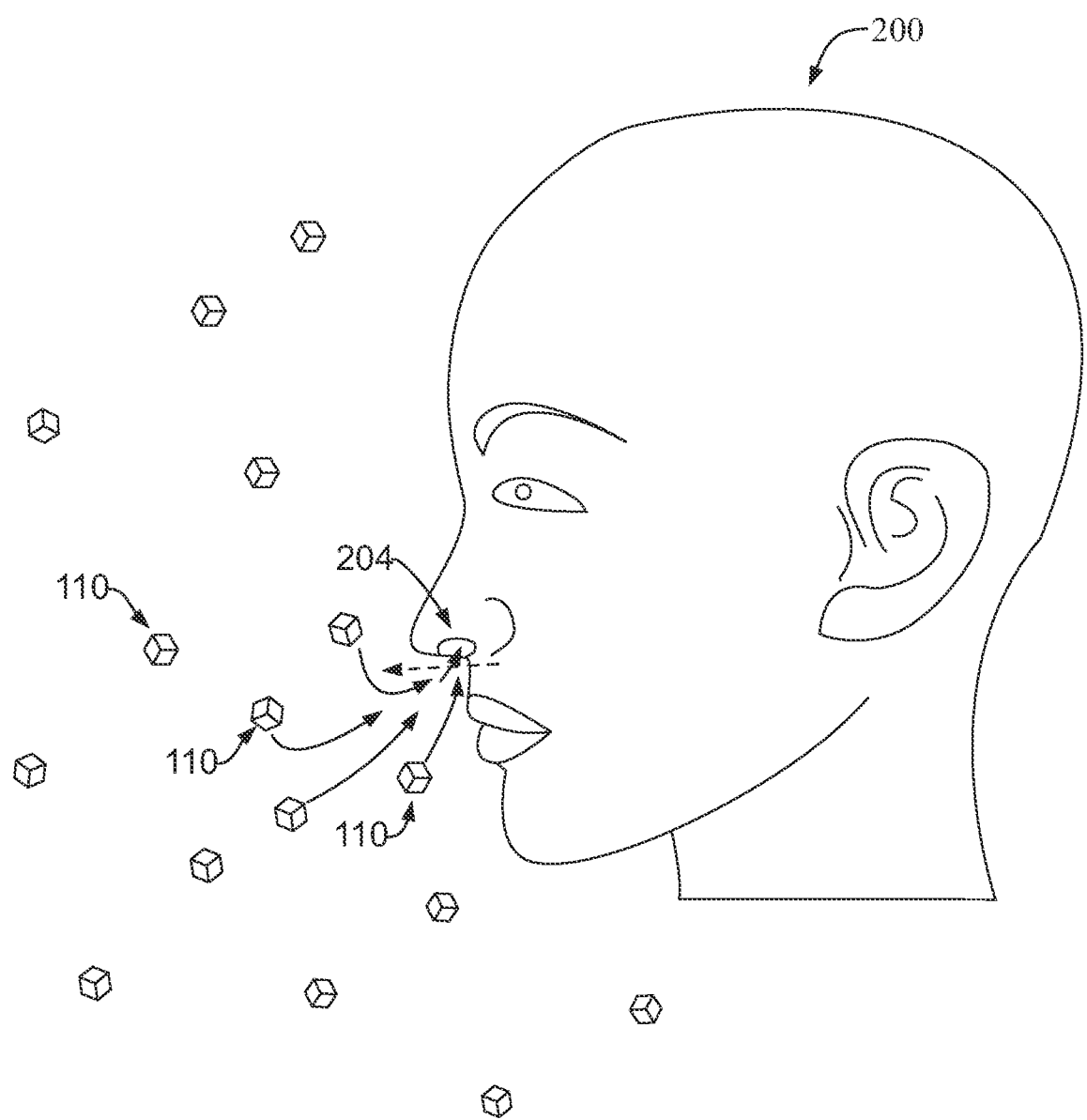
FIG. 3 presents an exemplary illustration of a person inhaling the salt particles dispensed in the air during the halotherapy session.
Figure 6:
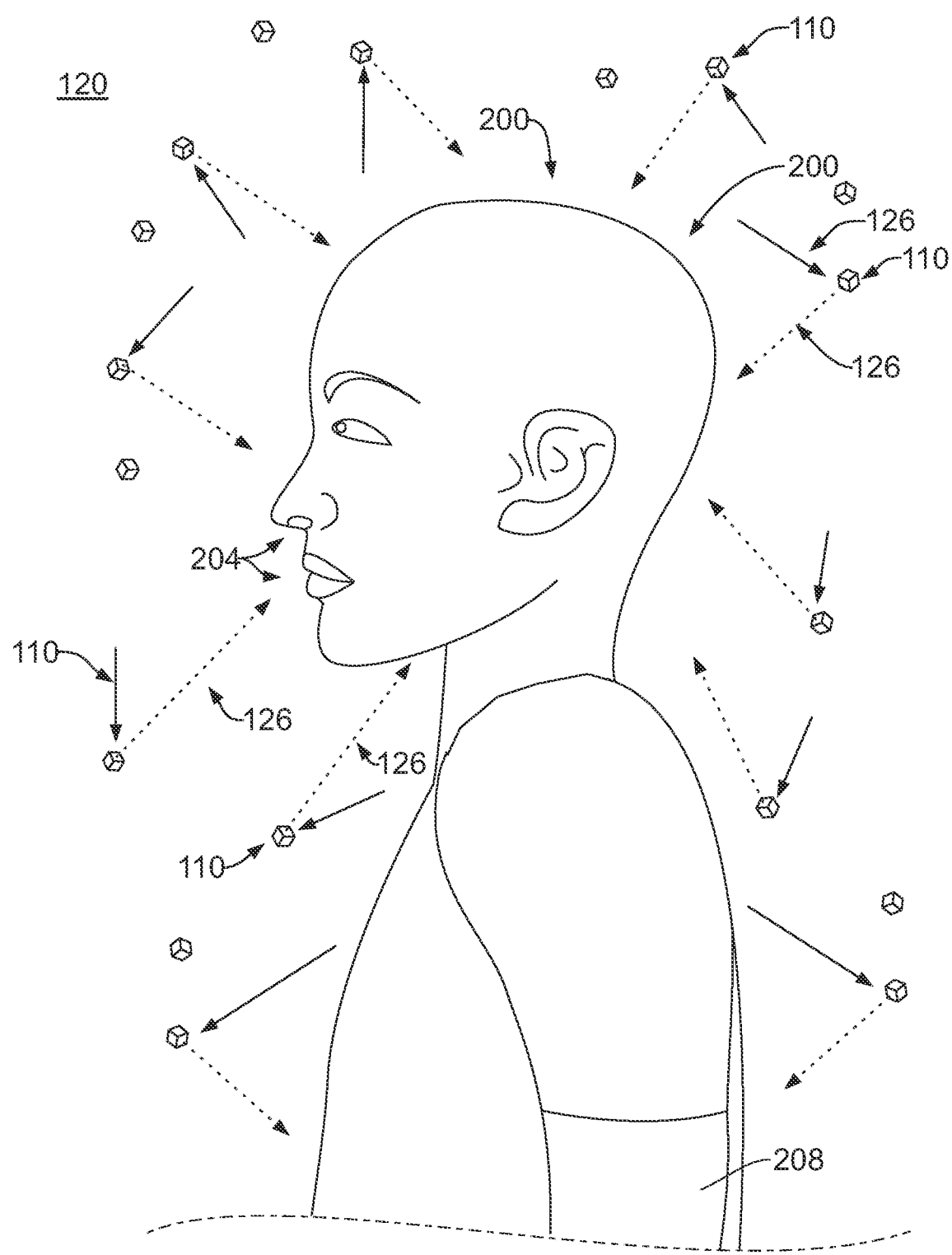
FIG. 6 presents a side view of salt particles dispensed in the air and refracting light waves toward the person inside of the enclosed space during a halotherapy session in accordance with the system and method of use of the present invention.

The machine 102 of the halotherapy and red light system 100 may generally comprise a unit 104 having a back portion 112 and a front portion 114. The front portion 114 of the machine may include a control panel 106 that controls and operates the machine 102. The front portion 114 of the machine may also include at least one vent 108 (although the accompanying figures illustrate at least two). The machine 102 may include a receptacle, grinding mechanism, and a discharge mechanism/apparatus (e.g., a fan). The receptacle of the machine 102 is designed to hold salt crystals therein. The receptacle (not shown) may include a funnel that directs the salt crystals into the grinding mechanism of the machine. The grinding mechanism goes through the process of manipulating the salt crystals in the receptacle by grinding the salt crystals to the size of about one to about five micrometers to produce a dry salt aerosol 110. The salt aerosol is then released with the use of the discharge mechanism of the machine into the atmosphere of the enclosed space 120 through the at least one vent 108 on the unit 104. As shown in FIGS. 3 and 6, the salt aerosol particles 110 dispersed into the air inside of the enclosed space 102 are absorbable by a person when the particles 110 land on the person's skin 202. The salt particles 110 are also inhalable by the person 200 when they breathe in air through their nose and mouth 204, which transports the salt particles into the person's respiratory system.

The machine 102, as is shown in FIG. 1, may comprise a freestanding unit that draws power from a power source, such as a domestic electrical outlet supplying 120v, or a generator (if the enclosed space is transportable). Alternatively, the machine 102 may comprise a unit 104 that is attachable to a designated wall space in the enclosed space 102. For example, the back portion 112 of the unit 104, in one exemplary embodiment, may be seated inside of a recess provided on one of the upstanding sidewalls 126 of the enclosed space 102. In this configuration, the machine 102 is not touching the base 128 of the enclosed space 120 taking up unnecessary space, thereby giving the person 200 inside the enclosed space 120 more room to move about. Although the present illustrations only show one machine 102 inside of the enclosed space 120 during a therapy session, one will appreciate that a plurality of machines may be disposed inside of the enclosed space if deemed necessary. For instance, where the enclosed space is too large for a single machine, additional machines may be added to ensure the airborne salinity level in the enclosed space is at an optimal level.

With reference to FIG. 2, the red light system 115 of the halotherapy and red light system 100 may include a plurality of red light devices 116 disposed about the ceiling 124 of the enclosed space 120. The red light devices 116 may also be evenly spaced-apart or scattered in a discernable or undiscernible pattern about the ceiling 124. Moreover, each red light device may be either recessed into the ceiling of the enclosed space or slightly protrude outwardly from the ceiling, as is shown in the FIG. 2. In an alternative embodiment, red light devices 116 may be disposed about the ceiling 124 and upstanding sidewalls 126 of the enclosed space 120 in a spaced-apart relationship (not shown). A red light device 116 may comprise a unit body 118 and at least one LED 122, with each body 118 including a set of connection cables that can connect one unit 118 to another unit 118 to allow each unit to be simultaneously controlled through a single device, such as a remote or switch. For instance, as shown in FIG. 2, all of the red light devices 116 may be simultaneously activated or deactivated through a control device to activate the unit's LED's 122. The LEDs 122 of each device 118 are capable of emitting red light beams 126. The red light beams 126, in one exemplary embodiment, may include a wavelength beam within a range of about 630 nm (i.e., red light) to about 850 nm (i.e., infrared light). One will appreciate, however, that alternative light spectrums that have beneficial effects may be used in the present invention. As will be appreciated, the number of red light devices 116 in the red light system 115 will vary depending on the size of the enclosed space 120 and thus, the number of devices 118 could range in numbers between one and about twenty or more devices.

With continued reference to FIG. 2, the halotherapy and red light system 100 may further include at least one physical exertion device 140. They physical exertion device 140 can be placed inside of the enclosed space 120 to allow a person 200 to naturally, through the use of the physical exertion device, increase their breathing and heart rate and the amount of air they inhale while the person spends time inside of the enclosed space 120. By using the physical exertion device 140, a person will naturally be inclined to take deeper breaths as the body's natural response to exercise is to bring in more oxygen to feed the respiratory system when burning fuel during exercise sessions. As a result, the person 200 inhales more salt particles 110 during a single therapy session than the person would have otherwise inhaled (if the person's heart rate remained the same). In one exemplary form, the at least one physical exertion device 140 may include fitness equipment, such as dumbbells or weight training devices, stationary bike, treadmill, elliptical machine, exercise ring, or the like. The enclosed space 120 may also provide a designated area that is large enough to allow the person to exercise by engaging in push up exercises, sit-ups, or pull-ups.

Referring now to FIGS. 3-6, in a therapy session, the machine 102 disperses salt particles 110 into the air inside of the enclosed space 120. Simultaneously, each red light device 116 of the red light system 115 will disperse red light beams 126 into the enclosed space 120. While a person undergoes a therapy session, which could last anywhere between ten minutes to about forty-five minutes or more, a person will inhale salt particles 110 infused with the surrounding air inside of the enclosed space. A person will also some of the salt particles 110 through their exposed skin 202 as salt particles will undoubtable land on the person.

A person 200 will also be subjected to the red light beams 126 that are emitted from the red light devices 116 of the red light system 115. Naturally, some of the red light beams 126 will be absorbed by the person's skin 202 when an unimpeded beam travels from the device's LED 122 to the person. Some red light beams, however, will be reach a person because of refraction. For instance, the combination of red light beams and halotherapy in the same enclosed space 120 produces a refractory phenomenon whenever a red light beam 126 makes contact with a salt particle 110. For example, when a beam of light travels between two media having different refractive indices, the beam undergoes refraction, and changes direction when it passes from the first medium to the second one. Wave theory also postulates that a small portion of each angled wave front should impact the second medium before the rest of the front reaches the interface. Meaning, a portion will start to move through the second medium while the rest of the wave is still traveling in the first medium, but will move more slowly due to the higher refractive index of the second medium. Because the wave front is now traveling at two different speeds, the wave will bend in to the second medium and thus, changing the angle of propagation. Whenever a beam is refracted or disturbed in some manner, some portion of the beam may be absorbed by the medium that caused the change of angle of propagation.

Figure 4:
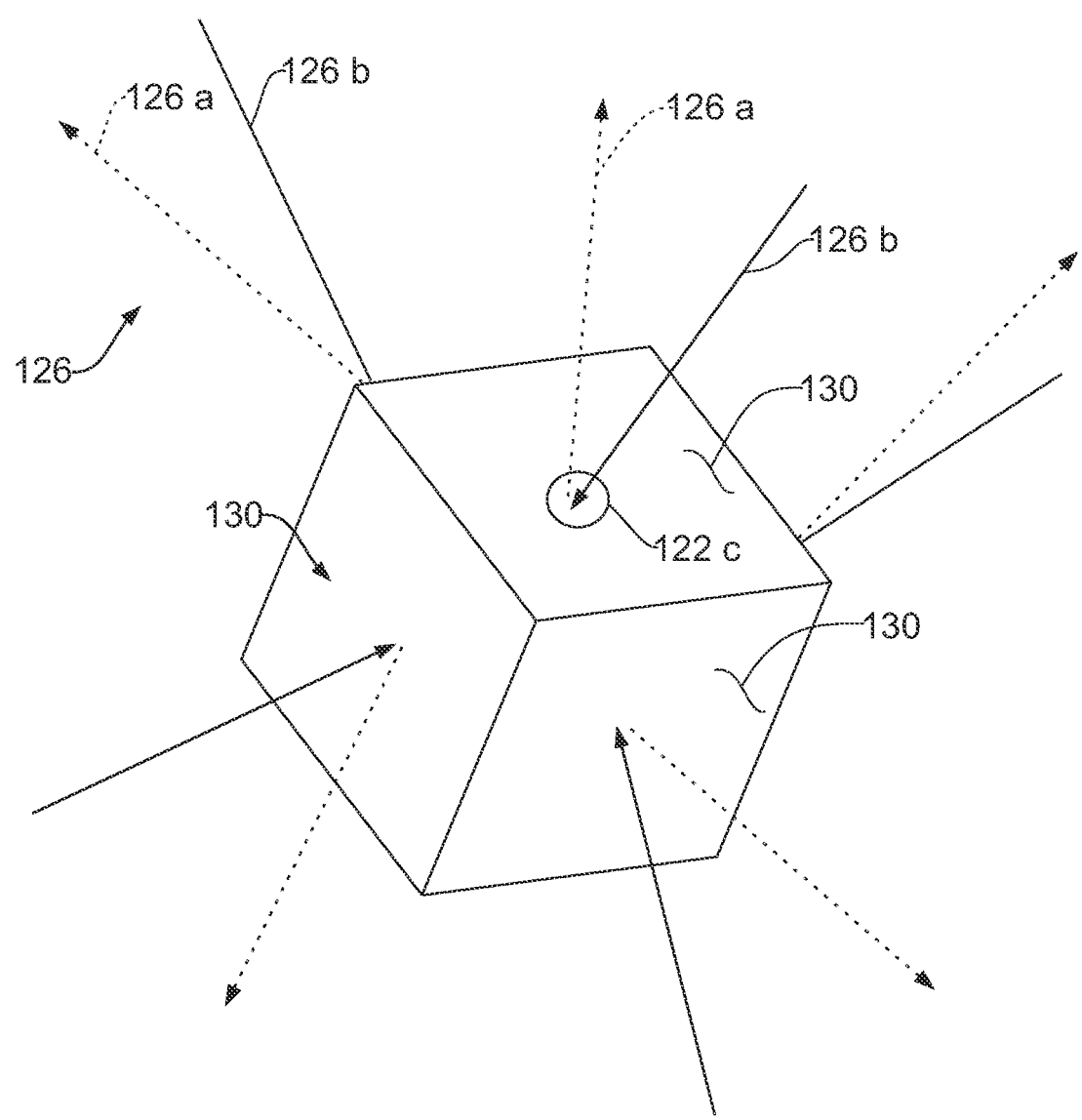
FIG. 4 presents an exemplary illustration of a plurality of light waves refracting off of a salt particle dispensed in the air.

Accordingly, in FIG. 4 a plurality of red light beams 122 are shown traveling through the air in the enclosed space 120 until making contact with the surface area 130 of a single salt particle 110. When the front portion 126a of the light beam 126 makes contact with the surface area 130 of the salt particle 110, the front portion 126a of the light beam 126 bends and changes direction, while the second portion 126b of the beam tries to catch up. A portion 126c of the light beam 126 may be lost to absorption by the salt particle 110 as the light beams 126 refract. Referring quickly to FIG. 2, generally the red light devices 116 disposed about the ceiling 124 or upstanding sidewall project red light beams 126 in a singular direction (i.e., the direction the LEDs 122 are facing). Meaning, certain parts of the person 200 that are not exposed or are otherwise sheltered from the direct pathway of the red light beams 126 will not make contact with red light beams. In the present invention, however, the halotherapy and red light system is designed to create multi-dimensional dispersions of red light waves 126 inside of an enclosed space 120.

The salt particles 110 are not stationary or uniform in shape and size and thus, each salt particle 110 may rotate and change its position as it moves through the air in the enclosed space 120. FIG. 6 shows how the red light beams 126 refract from a salt particles 110 rotating in the air in the enclosed space 120. When the red light beam makes contact with the salt particle, the trajectory of the red light beam changes and reaches areas that the red light beam would not have otherwise been able to reach. For example, red light beams 126 may reach an area or a number of areas that are for the most part hidden or inaccessible to the red light devices 116 that are disposed about the ceiling and upstanding sidewalls of the enclosed space. These areas include, but are not limited to, the person's chin, torso, arms, and neck. In the present invention, however, the red light beams refract from the salt particles 110 and reach those areas. Because there are thousands of salt particles 110 randomly floating within the enclosed space 120, different patterns emerge whenever a red light beam 126 makes contact with a salt particle, creating a diverse, multi-angled refractory dispersion phenomenon of red light beams inside of the enclosed space 120.

Figure 5:
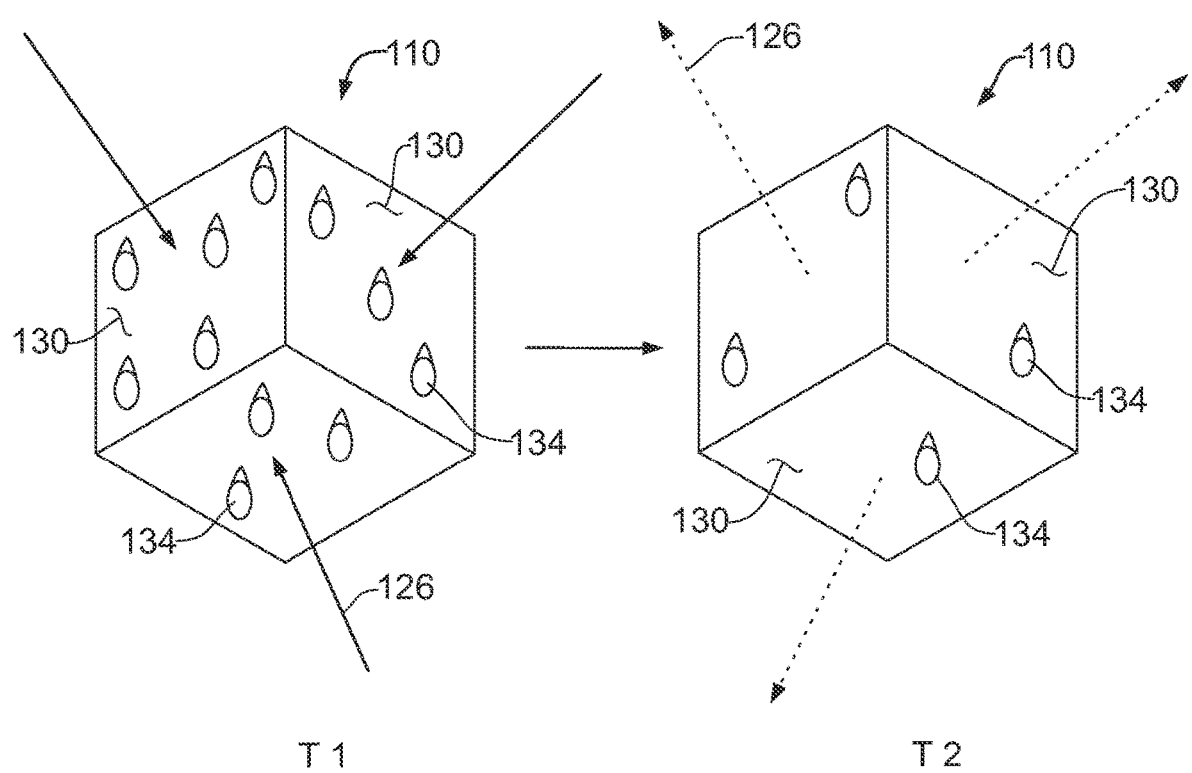
FIG. 5 presents an exemplary illustration of light waves colliding with salt particles dispensed in the air, reducing the amount of moisture in the salt particle.

With reference to FIG. 5, when a red light beam 126 makes contact with a salt particle, a portion of the red light beam 126 may be lost to the salt particle 110. When this occurs, the temperature T1 of the salt particle 110 begins to rise as the salt particle continues to absorb portions of red light beams 126. As the temperature T1 of the salt particle 110 rises to a higher temperature T2, the moisture 134 within the salt particle 110 begins to lessen. This in turn causes the salt particle 110 to become dryer, which enhances the therapeutic properties of the salt particle that are inhaled by the person 200. Moreover, portions of the red light beam 126 that are absorbed by the salt particle 110 may be released inside of the internal system of the person when a person inhales the salt particle 110. As such, the benefits of red light therapy may also be applied to the internal system of the person.

In summary, during a therapy session a person will inhale dry salt particles (with little to no moisture). The salt particles will reach the internal system of the person, including their nasal cavities, sinus cavities, ear canals, and other internal areas of the human body. For example, salt particles inhaled enter the person's respiratory system and dissolve in the lungs of the person, potentially killing portions of virus or bacteria lurking in the lungs. The salt particles may also come into contact with the person's skin and can absorb bacteria and other impurities responsible for many skin conditions. In an alternative embodiment, the halotherapy and red light system may include a machine comprising a halo unit hanging from the ceiling of the enclosure. One will appreciate that the invention described may also be used to therapeutically treat animals, such as dogs, cats, and horses. Overall, the present invention augments and enhances the positive effects of the red light therapy and halotherapy inside of an enclosed space.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A halotherapy enclosure, comprising:
   a plurality of upstanding side walls delimiting an enclosed space sufficiently sized to receive at least one physical exertion element;
   at least one salt aerosol discharge system including a grinder and a blower,
      wherein the grinder is configured to grind salt crystals into dispersible salt particles and the blower is configured to disperse the salt particles into the enclosed space;
   at least one red light device disposed within the enclosed space, the red light device configured to emit a plurality of red light waves for therapeutic benefit; and
   at least one controller in electronic communication and configured to control the red light device or the salt aerosol discharge apparatus.

2. The halotherapy enclosure of claim 1, wherein the controller, the grinder and the discharge blower of the salt aerosol discharge system are housed together in a housing body.

3. The halotherapy enclosure of claim 2, wherein the housing body is removably disposed within the enclosed space.

4. The halotherapy enclosure of claim 1, wherein the at least one red light device is disposed on at least one upstanding sidewall.

5. The halotherapy enclosure of claim 1, wherein the red light device includes one or more LEDs configured to emit wavelength beams within a range of about 660 nm to about 850 nm.

6. The halotherapy enclosure of claim 1, wherein the physical exertion element includes an exercise device, exercise fixture, or exercise machine.

7. The halotherapy enclosure of claim 1, wherein the halotherapy enclosure further comprises a plurality of sensors that measure humidity, temperature, and airborne salinity levels inside of the enclosed space.

8. The halotherapy enclosure of claim 1, wherein the halotherapy enclosure is ventilated.

9. A method for doing halotherapy, comprising the steps of:
   providing an enclosure comprising,
      a plurality of upstanding side walls delimiting an enclosed space sufficiently sized to receive at least one physical exertion element,
      a salt aerosol device comprising a housing that houses a grinder configured to grind salt crystals into dispersible salt particles, and at least one discharge apparatus including a blower in communication with the grinder that is configured to disperse the salt particles into the enclosed space,
      at least one red light device disposed within the enclosed space, the red light device configured to emit a plurality of red light waves for therapeutic benefit; and
      at least one controller in electronic communication and configured to control the red light device or the salt aerosol device, and
   exercising inside the enclosed space of the enclosure full of dispersed salt particles and red light waves.

10. The method of claim 9, wherein the at least one red light device is disposed on at least one upstanding sidewall.

11. The method of claim 9, wherein the red light device includes one or more LEDs configured to emit wavelength beams within a range of about 660 nm to about 850 nm.

12. The method of claim 9, wherein the salt aerosol device is removably disposed within the enclosed space.

13. The method of claim 9, wherein the physical exertion element includes an exercise device, exercise fixture, or exercise machine.

14. The method of claim 9, wherein the enclosure comprises a transportable structure.

15. The method of claim 9, wherein the enclosure is ventilated.

16. A method for doing halotherapy, comprising the steps of:
   providing a booth comprising,
      a plurality of upstanding side walls delimiting an enclosed space sufficiently sized to receive at least one physical exertion element,
      wherein the physical exertion element includes an exercise device, exercise fixture, or exercise machine, a salt aerosol discharge device comprising a housing that houses a grinder configured to grind salt crystals into dispersible salt particles, and at least one discharge apparatus including a blower in communication with the grinder that is configured to disperse the salt particles into the enclosed space, a plurality of red light devices disposed within the enclosed space, the red light devices configured to emit a plurality of red light waves for therapeutic benefit, and at least one controller in electronic communication and configured to control the red light device or the salt aerosol device;

activating the salt aerosol device and the red light device to respectively disperse salt particles into the enclosed space and emit the plurality of red light waves within the enclosed space; and exercising inside the enclosed space of the booth.

17. The method of claim 16, wherein the red light devices are disposed on one or more upstanding sidewalls.

18. The method of claim 16, wherein the red light devices include one or more LEDs configured to emit wavelength beams within a range of about 660 nm to about 850 nm.

19. The halotherapy enclosure claim 16, wherein the salt aerosol device is removably disposed within the enclosed space.

20. The method of claim 16, wherein the booth is transportable.

* * * * *